(12) United States Patent
Karasawa

(10) Patent No.: US 8,588,564 B2
(45) Date of Patent: Nov. 19, 2013

(54) CONFOCAL OPTICAL SYSTEM

(75) Inventor: Satoshi Karasawa, Tokyo (JP)

(73) Assignee: Hoya Corporation, Tokyo (JP)

( * ) Notice: Subject to any disclaimer, the term of this patent is extended or adjusted under 35 U.S.C. 154(b) by 269 days.

(21) Appl. No.: 12/776,525

(22) Filed: May 10, 2010

(65) Prior Publication Data

US 2010/0290100 A1 Nov. 18, 2010

(30) Foreign Application Priority Data

May 13, 2009 (JP) .................................. 2009-116408

(51) Int. Cl.
*G02B 6/32* (2006.01)

(52) U.S. Cl.
USPC .................... 385/33; 385/15; 385/31; 385/39; 385/901

(58) Field of Classification Search
USPC .................... 385/15, 31, 33, 39, 901
See application file for complete search history.

(56) References Cited

U.S. PATENT DOCUMENTS

| | | | |
|---|---|---|---|
| 4,678,328 A * | 7/1987 | Craig et al. | 356/141.5 |
| 5,559,916 A * | 9/1996 | Terao et al. | 385/85 |
| 5,600,744 A | 2/1997 | Takahashi | |
| 6,975,898 B2 | 12/2005 | Seibel | |
| 7,068,878 B2 | 6/2006 | Crossman-Bosworth et al. | |
| 7,129,472 B1 | 10/2006 | Okawa et al. | |
| 7,223,232 B2 | 5/2007 | Mizuno | |
| 7,338,439 B2 * | 3/2008 | Kanai | 600/176 |
| 7,616,986 B2 | 11/2009 | Seibel et al. | |
| 2004/0254474 A1 | 12/2004 | Seibel et al. | |
| 2005/0052753 A1 | 3/2005 | Kanai | |

FOREIGN PATENT DOCUMENTS

| | | |
|---|---|---|
| JP | 50-153651 | 12/1975 |
| JP | 08-136772 | 5/1996 |
| JP | 08-145780 | 6/1996 |
| JP | 2001-174744 | 6/2001 |
| JP | 2004-177826 | 6/2004 |
| JP | 2004-271433 | 9/2004 |
| JP | 2005-080769 | 3/2005 |
| JP | 2006-071549 | 3/2006 |
| JP | 2008-504557 | 2/2008 |
| JP | 2008-128730 | 6/2008 |

OTHER PUBLICATIONS

Japan Office action, dated Dec. 18, 2012 along with an english translation thereof.

* cited by examiner

*Primary Examiner* — Jennifer Doan
(74) *Attorney, Agent, or Firm* — Greenblum & Bernstein, P.L.C.

(57) ABSTRACT

A confocal optical system comprising a scanning fiber is provided. The scanning fiber is a single-mode fiber of which a first end is shaped as a curved surface. The scanning fiber transmits illumination light to the first end. The illumination light is emitted toward an observation area. The illumination light emanates from the first end. The illumination light emanates from the first end striking a target area within the observation area. The first end receives at least one of reflected light and fluorescence from the target area. The reflected light is the illumination light reflected from the target area. The fluorescence is induced at the target area by illumination from the illumination light.

16 Claims, 5 Drawing Sheets

CONFOCAL OPTICAL SYSTEM

BACKGROUND OF THE INVENTION

1. Field of the Invention

The present invention relates to a confocal optical system used for a scanning apparatus, such as a confocal endoscope apparatus, that can display a highly enlarged subject image at high resolution.

2. Description of the Related Art

Japanese Unexamined Patent Publication No. 2005-80769 discloses a confocal endoscope apparatus that can display a highly enlarged image at high resolution compared to a usual endoscope. In the confocal endoscope apparatus, a scanning fiber is moved along a predetermined course while emitting illumination light toward an observation area. Reflected light or autofluorescence from a point illuminated by the illumination light is made incident on the scanning fiber. The scanning fiber transmits the reflected light or autofluorescence to a light receiving unit, which detects the amount of received light.

To carry out a confocal observation with a confocal endoscope apparatus having the above structure, it is preferable to condense a beam of light with a thick diameter.

In addition, a single mode fiber should be used as the scanning fiber in a confocal observation. However, it is difficult to emit a beam with a sufficiently large diameter from a single mode fiber. Accordingly, a lens unit mounted in the emission end of the scanning fiber needs to include an optical enlargement system.

However, the size of the lens unit increases by including the optical enlargement system. In addition, movement of a point illuminated by the illumination light according to the movement of the emission end of a scanning fiber with the optical enlargement system is much less than it is relative to a scanning fiber without the optical enlargement system. In order to capture an image of a subject of considerable size, the emission end needs to be moved substantially. Accordingly, it is difficult to manufacture a thin insertion tube that includes the above lens unit and scanning fiber.

SUMMARY OF THE INVENTION

Therefore, an object of the present invention is to provide a confocal optical system that enables the entire lens unit to be downsized to fit inside a thin insertion tube.

According to the present invention, a confocal optical system, comprising a scanning fiber is provided. The scanning fiber is a single-mode fiber of which a first end is shaped as a curved surface. The scanning fiber transmits illumination light to the first end. The illumination light is emitted toward an observation area. The illumination light emanates from the first end. The illumination light emanates from the first end striking a target area within the observation area. The first end receives at least one of reflected light and fluorescence from the target area. The reflected light is the illumination light reflected from the target area. The fluorescence is induced at the target area by illumination from the illumination light.

Further, the first end is shaped so that a numerical aperture of the first end is greater than that of the single-mode fiber.

Further, a portion of the single-mode fiber within a mode field diameter at the first end is shaped as a spherical surface. Another portion of the single-mode fiber between the mode field diameter and an outside diameter at the first end is shaped as a conical surface.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
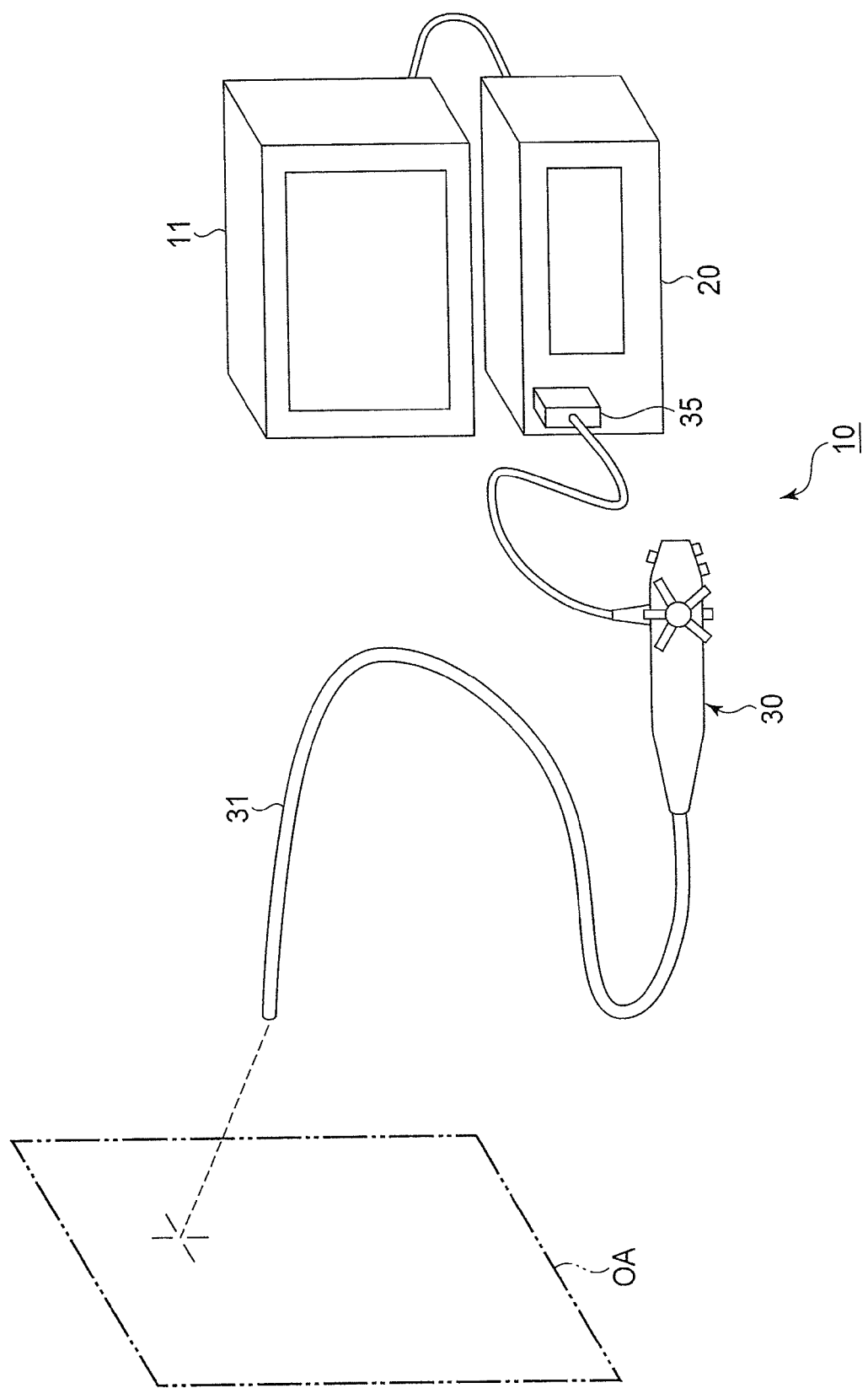
FIG. 1 is a schematic diagram of a confocal endoscope apparatus comprising a confocal optical system of the embodiments of the present invention.

The present invention is described below with reference to the embodiment shown in the drawings.

In FIG. 1, the confocal endoscope apparatus 10 comprises a confocal endoscope processor 20, a confocal endoscope 30, and a monitor 11. The confocal endoscope processor 20 is connected to the confocal endoscope 30 and the monitor 11.

The confocal endoscope processor 20 provides excitation light that is shined on an observation area (see "OA" in FIG. 1). The excitation light produced by the confocal endoscope processor 20 is transmitted to the distal end of the insertion tube 31 of the confocal endoscope 30 and emitted towards one point in the observation area. Fluorescence from the point struck by the excitation light is transmitted from the distal end of the insertion tube 31 to the confocal endoscope processor 20.

An emission direction, which is the direction in which the excitation light is emitted from the insertion tube 31, is changed by an actuator (not depicted in FIG. 1) mounted in the distal end of the insertion tube 31. By varying the emission direction the observation area is scanned with the excitation light emitted from the illumination fiber. The actuator is controlled by the confocal endoscope processor 20.

The confocal endoscope processor 20 determines the emission direction based on the control status of the actuator. The confocal endoscope processor 20 receives fluorescence corresponding to the emission direction, and generates a pixel signal according to the quantity of fluorescence received. One frame of an image signal is generated from pixel signals corresponding to the illuminated points dispersed throughout the observation area. The generated image signal is transmitted to the monitor 11, upon which an image corresponding to the received image signal is displayed.

Figure 2:
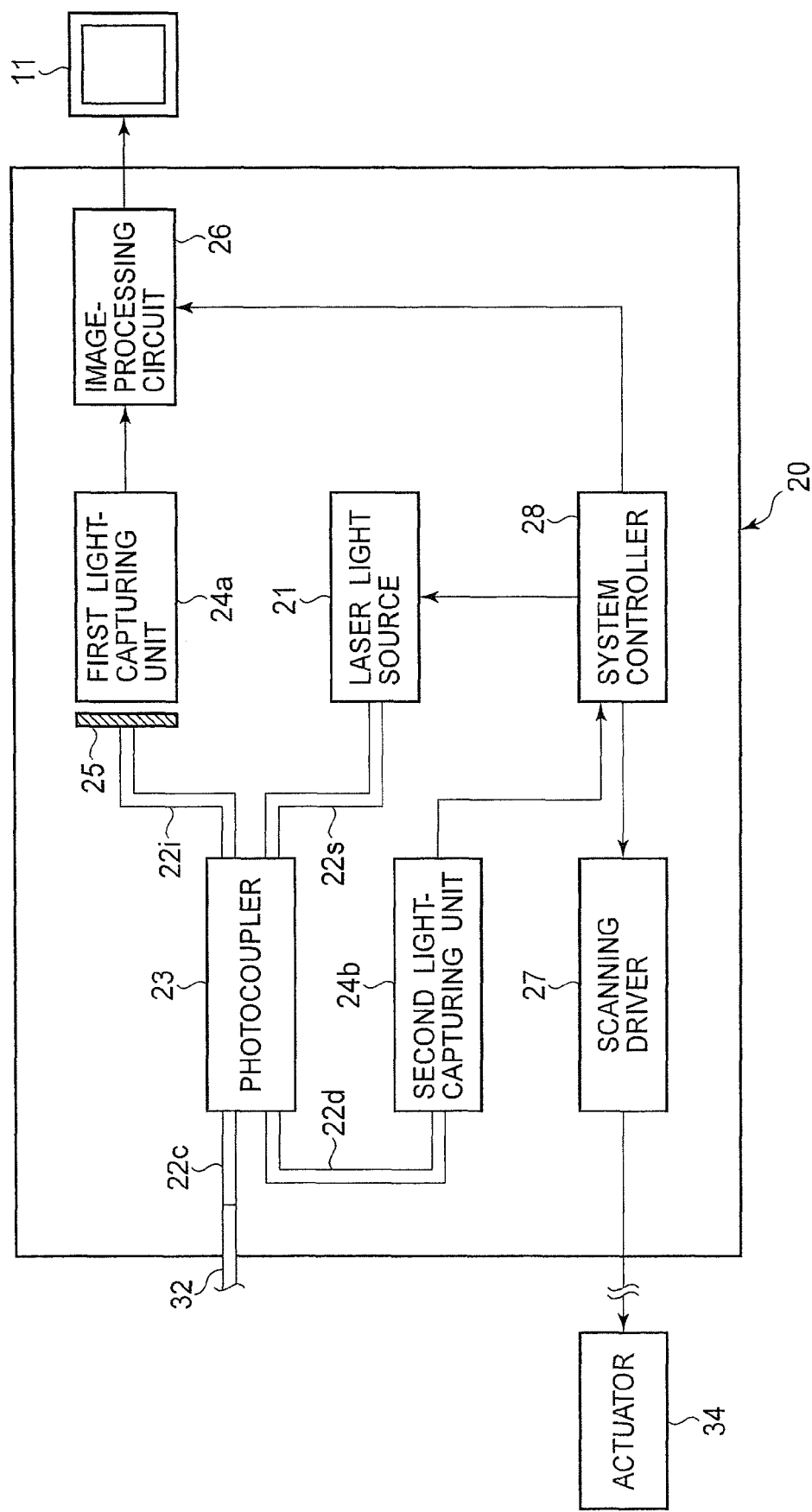
FIG. 2 is a block diagram schematically showing the internal structure of the confocal endoscope processor.

As shown in FIG. 2, the confocal endoscope processor 20 comprises a laser light source 21, a supply-fiber 22s, a connection-fiber 22c, an image-transmission fiber 22i, a detection-fiber 22d, a photocoupler 23, first and second light-capturing units 24a and 24b, an excitation light cut filter 25, an image-processing circuit 26, a scanning driver 27, a system controller 28, and other components.

Excitation light, which causes certain types of subjects, such as human organs, to fluoresce, is generated by the laser light source 21. The laser light source 21 is optically connected to the supply fiber 22s. The excitation light from the laser light source 21 is transmitted to the supply-fiber 22s.

The supply-fiber 22s is optically connected to both the connection-fiber 22c and the detection-fiber 22d by the photocoupler 23. Light can be transmitted between the supply-fiber 22s and the connection-fiber 22c and detection-fiber 22d.

In addition, the connection-fiber 22c and the detection fiber 22d are also optically connected to the image-transmission fiber 22i by the photocoupler 23. Light can be transmitted between the image-transmission fiber 22i and the connection-fiber 22c and detection-fiber 22d.

The photocoupler 23 is a four-port directive coupler. The excitation light transmitted from the supply-fiber 22s is divided and routed into the connection-fiber 22c and the detection-fiber 22d. The reflection light and fluorescence transmitted from the connection fiber 22c is divided and routed into the image-transmission fiber 22i and the supply-fiber 22s.

The detection fiber 22d is optically connected to the second light-capturing unit 24b. The excitation light routed to the detection-fiber 22d is transmitted to the second light-capturing unit 24b.

The second light-capturing unit 24b detects the amount of the excitation light. The detected amount of excitation light is communicated to the system controller 28, which controls the amount of excitation light generated by the laser light source 21 based on the amount of detected light.

The connection-fiber 22c is optically connected to the proximal end of the scanning fiber 32 mounted in the confocal endoscope 30. The excitation light routed into the connection-fiber 22c is transmitted through the scanning fiber 32 to the distal end of the insertion tube 31, from which it is emitted. In addition, as described later, reflected light and fluorescence are transmitted from the distal end to the connection-fiber 22c by the scanning fiber 32.

As described above, the reflected light and fluorescence transmitted to the connection fiber 22c is divided and routed into the image-transmission fiber 22i and the supply-fiber 22s by the photocoupler 23. The image-transmission fiber 22i is optically connected to the first light-capturing unit 24a. The excitation light cut filter 25 is mounted between the image-transmission fiber 22i and the first light-capturing unit 24a.

The reflected light, which is excitation light that has traveled through the image-transmission fiber 22i, is attenuated by the excitation light cut filter 25 and prevented from entering the first light-capturing unit 24a. On the other hand, the fluorescence that travels through the image-transmission fiber 22i passes through the excitation light cut filter 25 and enters the first light-capturing unit 24a.

The first light-capturing unit 24 generates a pixel signal according to the amount of fluorescence detected from a point in the observation area that has been illuminated by the excitation light. The pixel signal is transmitted to the image-processing circuit 26, which stores the pixel signal in an image memory (not depicted).

As described later, after pixel signals corresponding to a succession of points dispersed throughout the observation area that have been illuminated by the moving excitation light are generated and stored in the image memory, the image-processing circuit 26 carries out predetermined signal processing on the pixel signals, and then one frame of the image signal is transmitted to the monitor 11.

Figure 3:
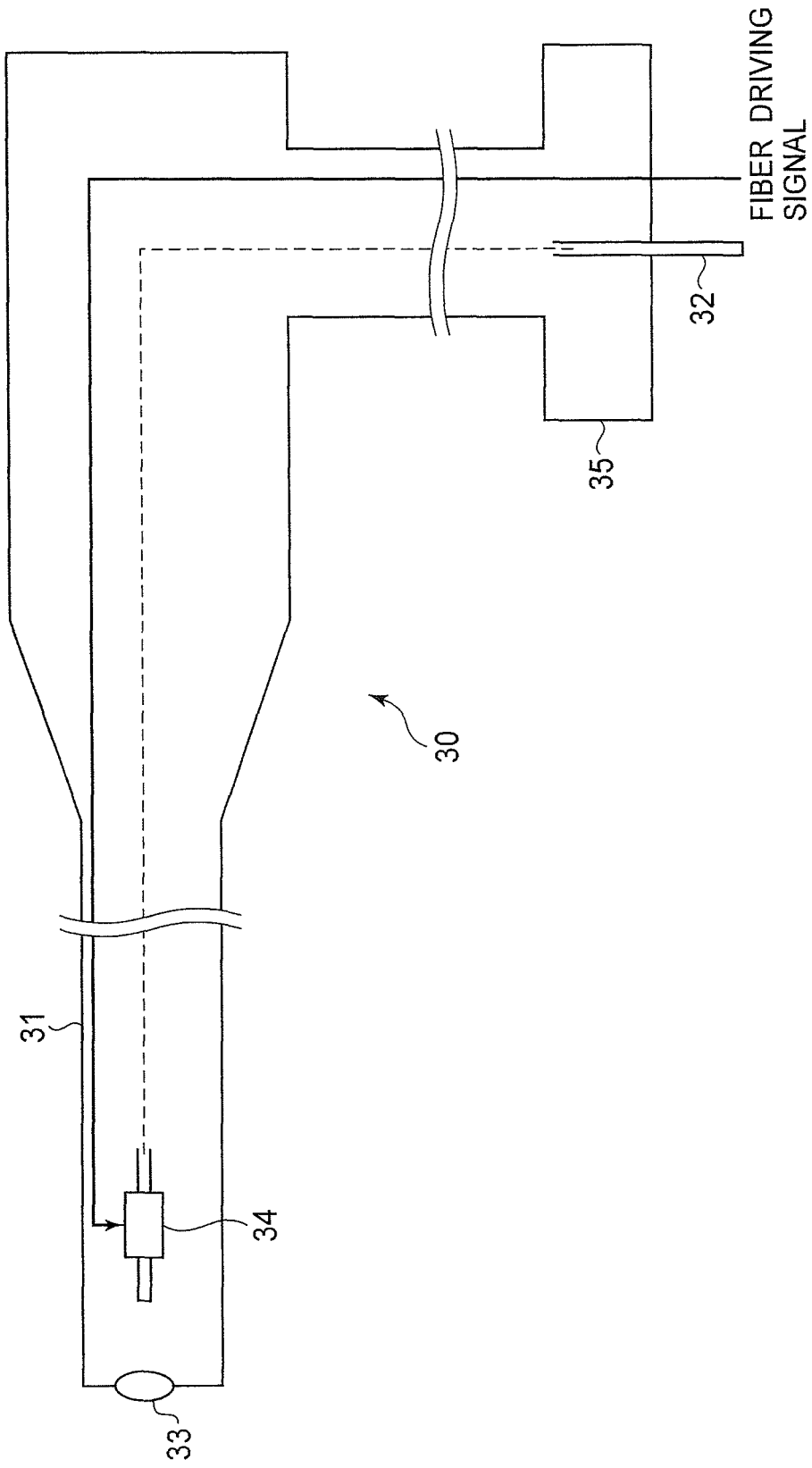
FIG. 3 is a block diagram schematically showing the internal structure of the confocal endoscope.

Next, the structure of the confocal endoscope 30 is explained. As shown in FIG. 3, the confocal endoscope 30 comprises the scanning fiber 32, a lens unit 33, the actuator 34, and other components.

The scanning fiber 32 is arranged inside the confocal endoscope 30 from the connector 35 to the distal end of the insertion tube 31. As described above, the excitation light generated by the laser light source 21 is transmitted to the proximal end of the scanning fiber 32 via the supply-fiber 22s, the photocoupler 23, and the connection-fiber 22c. The excitation light made incident on the proximal end is transmitted to the distal end, from which it is emitted toward a subject.

Figure 4:
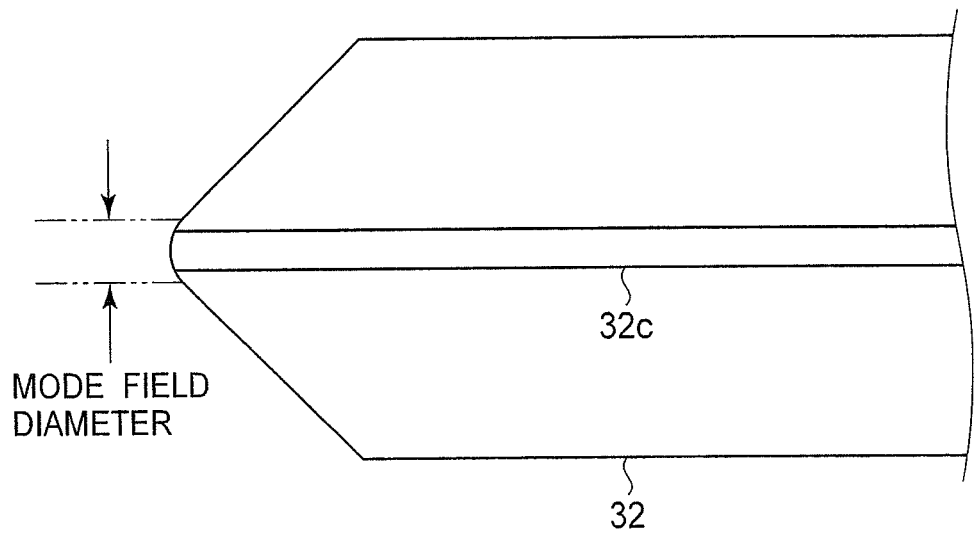
FIG. 4 is an enlarged diagram of the emission end of the scanning fiber.

A single-mode fiber is used for the scanning fiber 32. In addition, the emission end of the scanning fiber 32, which is arranged inside of the distal end of the insertion tube 31, has been ground so that the portion of the emission end inside the mode field diameter, whose center coincides with a core 32c, has a spherical surface, as shown in FIG. 4. In addition, the spherical surface is shaped so that the numerical aperture at the emission end is greater than that of the single-mode fiber in use. Accordingly, the end of the scanning fiber 32 is a "lens-ed" fiber.

Generally, the diameter of a beam emitted from a single-mode fiber is not thick enough to use for confocal observation because the numerical aperture of the single-mode fiber is too small. However, because the emission end of the scanning fiber 32 is shaped as a spherical surface as described above, the beam of emitted excitation light has a diameter that is thick enough to use for in a confocal observation.

The actuator 34 is mounted near the emission end of the scanning fiber 32. The actuator 34 moves the emission end of the scanning fiber 32 based on a fiber driving signal transmitted from the scanning driver 27 so that the emission end of the scanning fiber 32 traces a predetermined course, such as a spiral course. By emitting the excitation light from the moving emission end of the scanning fiber 32, the observation area is scanned with the excitation light.

The lens unit 33 is mounted in the downstream direction of the excitation light from the emission end of the scanning fiber 32. The lens unit 33 has a condenser optical system. Accordingly, the excitation light emitted from the emission end of the scanning fiber 32 is condensed by the lens unit 33, and directed towards a point in the observation area.

Even though the excitation light is directed towards one fine point, a peripheral area surrounding the point is illuminated with the excitation light due to diffraction limited so that the amount of the excitation light is distributed according to Gaussian distribution.

Excitation light is reflected and fluoresced from every point struck by the excitation light, but only the portion of the reflected light and fluorescence that emanates from the targeted points' central pinpoint areas, which are confocal points with respect to the emission end of the scanning fiber 32, is made incident on the emission end of the scanning fiber 32. The remaining portion of reflected light and fluorescence that emanates from within the targeted points but outside of the central pinpoint area is not made incident on the emission end.

The reflected light and fluorescence made incident on the emission end is transmitted to the proximal end of the scanning fiber 32. The reflected light and fluorescence is transmitted to the first light-capturing unit 24a via the connection-fiber 22c, the photocoupler 23, and the image-transmission fiber 22i. As described above, the reflected light, which is the excitation light, is blocked by the excitation light cut filter 25, so that only the fluorescence is made incident on the first light-capturing unit 24a.

In the above embodiment, a lens unit 33 can be downsized, the diameter of an insertion tube 31 can be reduced, and the signal-to-noise ratio can be improved. Those effects are explained as follows.

In a confocal observation, optical information from only a pinpointed area of each illuminated point needs to be captured. Accordingly, a single-mode fiber is adequate for the scanning fiber 32 used in the confocal endoscope apparatus. In addition, in a confocal observation a light beam with a thick diameter must be condensed by a condenser optical system that has a large numerical aperture.

Figure 5:
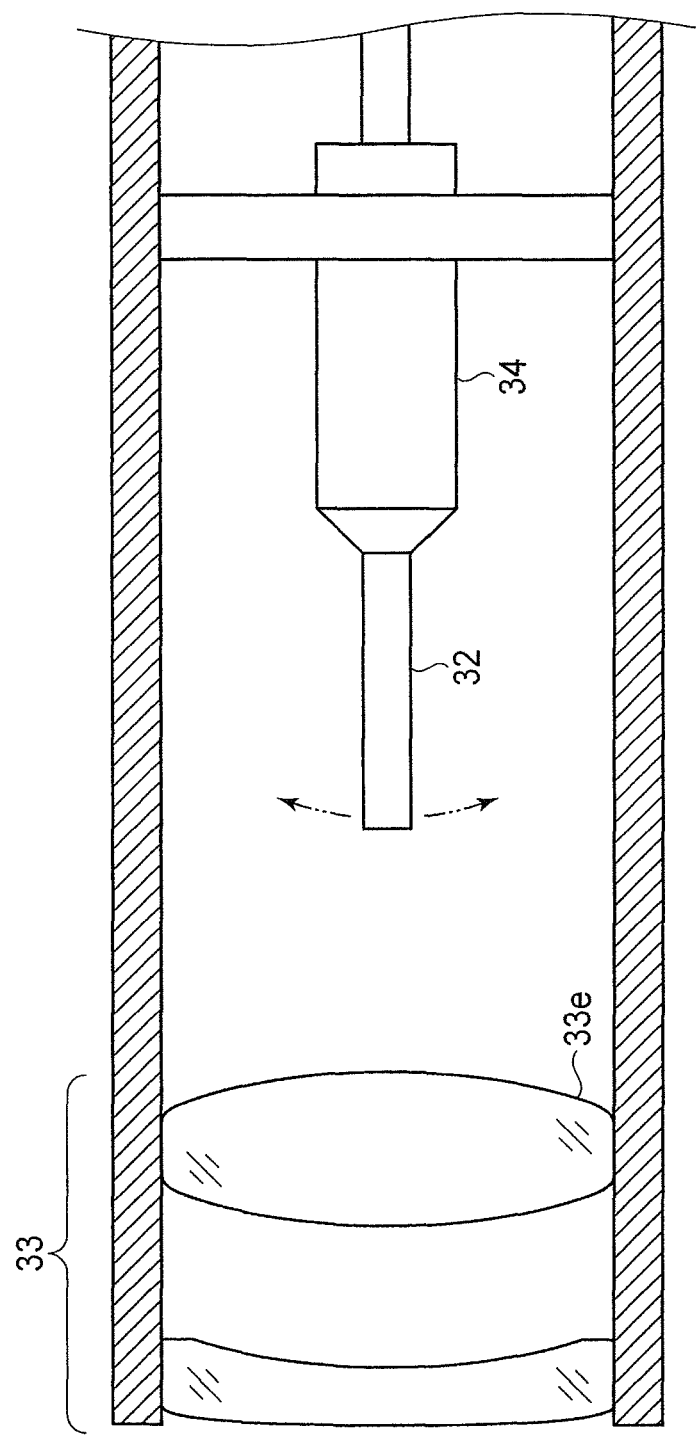
FIG. 5 is a cutaway view of a schematic structure near the emission end of the scanning fiber in a prior confocal endoscope.

As described above, the numerical aperture of a standard single-mode fiber is low, and the diameter of the beam of excitation light emitted from the single-mode fiber is not thick enough. Accordingly, as shown in FIG. 5, an optical enlargement system 33e that expands the diameter of the excitation light beam generally needs to be included in a lens unit 33.

On the other hand, in the above embodiment, because the diameter of the beam of excitation light emitted from the emission end of the scanning fiber 32 has adequate thickness, the optical enlargement system 33e is unnecessary. Consequently, a lens unit 33 can be downsized as a result of the omitted optical enlargement system 33e.

In addition, a mounted optical enlargement system 33e restricts the scope of a view angle. So, to capture an image with sufficient breadth, the emission end of the scanning fiber 32 needs to have a broad range of movement. The diameter of a tube (not depicted) around the scanning fiber 32 needs to be thick enough to enable a broad range of movement for the emission end. As a result, it is difficult to provide an insertion tube 31 with a thin diameter.

On the other hand, in the above embodiment, because the optical enlargement system 33e can be omitted, the breadth of the view angle is increased. As a result, the emission end has a broader range of motion than it would with an optical enlargement system 33e. Consequently, a thinner insertion tube 31 can be adopted relative to an apparatus equipped with the optical enlargement system 33e.

In addition, in order to generate an image with a high signal-to-noise ratio, light having bands other than fluorescence must be prevented from entering the first light-capturing unit 24a. However, not only fluorescence but also excitation light is emitted from the image-transmission fiber 22i. Although the excitation light is attenuated by the excitation light cut filter 25, as described above, it is difficult to block the excitation light. So, it is preferable to have only a minimal amount of excitation light transmitted by the image-transmission fiber 22i.

Generally, the excitation light transmitted to the image-transmission fiber 22i includes not only the excitation light reflected from the illuminated point in the observation area that is made incident on the emission end of the scanning fiber 32, but also includes excitation light that is partially reflected by the surface of the emission end of the scanning fiber 32.

In the above embodiment, a portion of the excitation light that is transmitted to the emission end is reflected in a direction that is inclined from the axis of the scanning fiber 32 because the emission end within the mode field diameter is shaped as a spherical surface. The excitation light reflected in the direction inclined from the axis cannot be transmitted to the proximal end because the reflected excitation light cannot meet the requirement of the core propagation mode. As a result, the amount of the excitation light transmitted to the image-transmission fiber 22i is mitigated. Finally, the signal-to-noise ratio can be improved.

The emission end of the scanning fiber within the mode field diameter is shaped as a spherical surface in the above embodiment. However, the emission end is not limited to the spherical surface. For example, the emission end can be shaped as a curved surface, such as an aspheric surface. The emission end within the field mode diameter can take on any shapes as long as the numerical aperture of the shaped emission end is greater than that of the original single-mode fiber.

The emission end is ground so that the emission end is shaped as a spherical surface in the above embodiment. However, the method for shaping the emission end is not limited to grinding. Of course, an end can be finely shaped by grinding, and a "lens-ed" fiber can be manufactured with a numerical aperture that is large enough relative to the lens unit 33 in use.

The emission end of the scanning fiber outside of the mode field diameter is shaped as a conical surface in the above embodiment. However, this portion can be shaped as a spherical surface similar to the portion within the mode field diameter.

The confocal optical system is adopted for a confocal endoscope apparatus in the above embodiment. However, the same effect can be achieved even if the confocal optical system is adopted for another scanning observation apparatus, such as a confocal probe, a multi-photon fluorescence microscope apparatus, or a second harmonic microscope apparatus.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2009-116408 (filed on May 13, 2009), which is expressly incorporated herein, by reference, in its entirety.

The invention claimed is:

1. A confocal optical system comprising:
    a scanning fiber defined as a single-mode fiber has a first end including a core shaped as a convex surface, an entire surface of the core including a three dimensionally arcuate surface,
    the scanning fiber transmitting illumination light to the first end,
    the illumination light being emitted toward an observation area,
    the illumination light emanating from the first end,
    the illumination light emanating from the first end striking a target area within the observation area, the first end receiving at least one of reflected light and fluorescence from the target area,
    the reflected light being the illumination light reflected from the target area, and
    the fluorescence being induced at the target area by illumination from the illumination light.

2. The confocal optical system according to claim 1, wherein the core is shaped so that a numerical aperture of the first end is greater than that of the single-mode fiber.

3. The confocal optical system according to claim 1, wherein the core, which is within a mode field diameter at the first end, is shaped as a spherical surface, and a portion of the single-mode fiber between the mode field diameter and an outside diameter at the first end is shaped as a conical surface.

4. The confocal optical system according to claim 1, wherein the first end has a surface that is shaped by grinding the single-mode fiber.

5. An optical system comprising:
    a scanning fiber defined as a single-mode fiber has a first end including a core shaped as a convex surface, an entire surface of the core including a three dimensionally arcuate surface,
    the scanning fiber transmitting illumination light to the first end,
    the illumination light being emitted toward an observation area,
    the illumination light emanating from the first end,
    the illumination light emanating from the first end striking a target area within the observation area,
    the first end receiving reflected light from the target area, and the reflected light being the illumination light reflected from the target area.

6. The optical system according to claim 5, wherein the core is shaped so that a numerical aperture of the first end is greater than that of the single-mode fiber.

7. The optical system according to claim 5, wherein the core, which is within a mode field diameter at the first end, is shaped as a spherical surface, and a portion of the single-mode fiber between the mode field diameter and an outside diameter at the first end is shaped as a conical surface.

8. The optical system according to claim 5, wherein the first end has a surface that is shaped by grinding the single-mode fiber.

9. The confocal optical system according to claim 1, wherein the convex surface of the core is shaped by grinding the single-mode fiber.

10. The confocal optical system according to claim 5, wherein the convex surface of the core is shaped by grinding the single-mode fiber.

11. The confocal optical system according to claim 1, the convex surface comprising a spherical surface.

12. The confocal optical system according to claim 1, the convex surface comprising an aspherical surface.

13. The optical system according to claim 5, the convex surface comprising a spherical surface.

14. The optical system according to claim 5, the convex surface comprising an aspherical surface.

15. The confocal optical system according to claim 1, wherein a mode field diameter is greater than a diameter of the core.

16. The optical system according to claim 5, wherein a mode field diameter is greater than a diameter of the core.

* * * * *